United States Patent [19]
Shieh

[11] Patent Number: 5,796,053
[45] Date of Patent: Aug. 18, 1998

[54] STETHOSCOPE STRUCTURE

[76] Inventor: Woei-Kang Shieh, 4F, No. 63, Hua Ling Street, Taipei, Taiwan

[21] Appl. No.: 905,500

[22] Filed: Aug. 4, 1997

[51] Int. Cl.$^6$ ............................................. A61B 7/02
[52] U.S. Cl. ............................... 181/131; 181/137
[58] Field of Search ........................ 131/131, 137; 381/67

[56] References Cited

U.S. PATENT DOCUMENTS 3,157,246  11/1964  Howell ................................ 181/137
4,167,223   9/1979  Liesse ................................. 181/131

FOREIGN PATENT DOCUMENTS 82209354  3/1982  Taiwan .

*Primary Examiner*—Khanh Dang
*Attorney, Agent, or Firm*—Ostrolenk, Faber, Gerb & Soffen, LLP

[57] ABSTRACT

A stethoscope includes a pair of binaurals and a chest piece with a rubber tube extending and connected therebetween. The chest piece has a body defining therein a cavity for movably receiving a frequency switching member which is movable between a first position and a second position. A retainer ring having a bore is fixed to the body to retain the frequency switching member within the cavity. The frequency switching member has a reduced end with a circumferential rib formed thereon extending through the bore of the retainer ring. The retainer ring has a circumferential rib which surrounds the bore and is in tight contact engagement with a membrane fixed to the body so as to define a first confined zone on the membrane which provides a first, low frequency vibration mode of the membrane. The frequency switching member is biased by a spring toward the first position where a projection formed on the frequency switching member partially extends out of the body through a through hole to be accessible by the user. The projection is depressible to have the frequency switching member move toward the second position, bringing the circumferential rib of the frequency switching member into contact engagement with the membrane so as to define a smaller confined zone on the membrane which provides a second, high frequency vibration mode of the membrane.

6 Claims, 3 Drawing Sheets

STETHOSCOPE STRUCTURE

FIELD OF THE INVENTION

The present invention relates generally to a stethoscope and in particular to a stethoscope having a chest piece which allows a quick switch between low and high frequency monitoring of the patient's body activity.

BACKGROUND OF THE INVENTION

Stethoscopes are a very useful tool for physician to diagnose a patient. In general, the stethoscope comprises a pair of binaurals to be worn on the ears of the physician and a chest piece to be placed on the chest or stomach of the patient to receive audio signal therefrom for diagnoses. A rubber tube connects the chest piece to the binaurals to transmit the audio signal obtained from the chest piece to the binaurals.

Placing the chest piece on for example the patient's chest allows a low frequency audio signal to be received from the patient' chest. To obtain a high frequency audio signal, the physician has to press the chest piece against the patient's body. This causes discomfort of the patient. Thus, a turret is provided on the stethoscope to allow a physician to select, between at least two chest pieces adapted to receive different frequencies, a desired one to receive the desired frequency from the patient's body. An example of such a turret type stethoscope is disclosed in Taiwan patent publication No. 82209354. Such a turret stethoscope allows a physician to obtain the audio signal of desired frequency range from the patient's body without pressing the chest piece against the patient's body. However, such a turret stethoscope has a disadvantage that the physician has to rotate the turret in order to select and use different chest pieces to listen to sounds of different frequencies, which takes certain times. Such a delay in time may be inconvenient and causes trouble for the physician.

It is therefore desirable to provide an improved stethoscope structure which provides a more efficient switching between two different frequencies.

SUMMARY OF THE INVENTION

The principal object of the present invention is to provide a stethoscope structure in which the chest piece is switchable between high frequency and lower frequency in a very efficient manner.

It is another object of the present invention to provide a stethoscope structure wherein a single chest piece is used to access different frequencies of audio signal from the patient's body so as to simplify the overall structure of the stethoscope.

To achieve the above objects, there is provided a stethoscope comprising a pair of binaurals and a chest piece with a rubber tube extending and connected therebetween. The chest piece has a body defining therein a cavity for movably receiving a frequency switching member which is movable between a first position and a second position. A retainer ring having a bore is fixed to the body to retain the frequency switching member within the cavity. The frequency switching member has a reduced end with a circumferential rib formed thereon extending through the bore of the retainer ring. The retainer ring has a circumferential rib which surrounds the bore and is in tight contact engagement with a membrane fixed to the body so as to define a first confined zone on the membrane which provides a first, low frequency vibration mode of the membrane. The frequency switching member is biased by a spring toward the first position where a projection formed on the frequency switching member partially extends out of the body through a through hole to be accessible by the user. The projection is depressible to have the frequency switching member move toward the second position, bringing the circumferential rib of the frequency switching member into contact engagement with the membrane so as to define a smaller confined zone on the membrane which provides a second, high frequency vibration mode of the membrane.

BRIEF DESCRIPTION OF THE DRAWINGS

The present invention will be better understood from the following description of a preferred embodiment of the present invention, with reference to the attached drawings, wherein.

DETAILED DESCRIPTION OF THE PREFERRED EMBODIMENT

Figure 1:
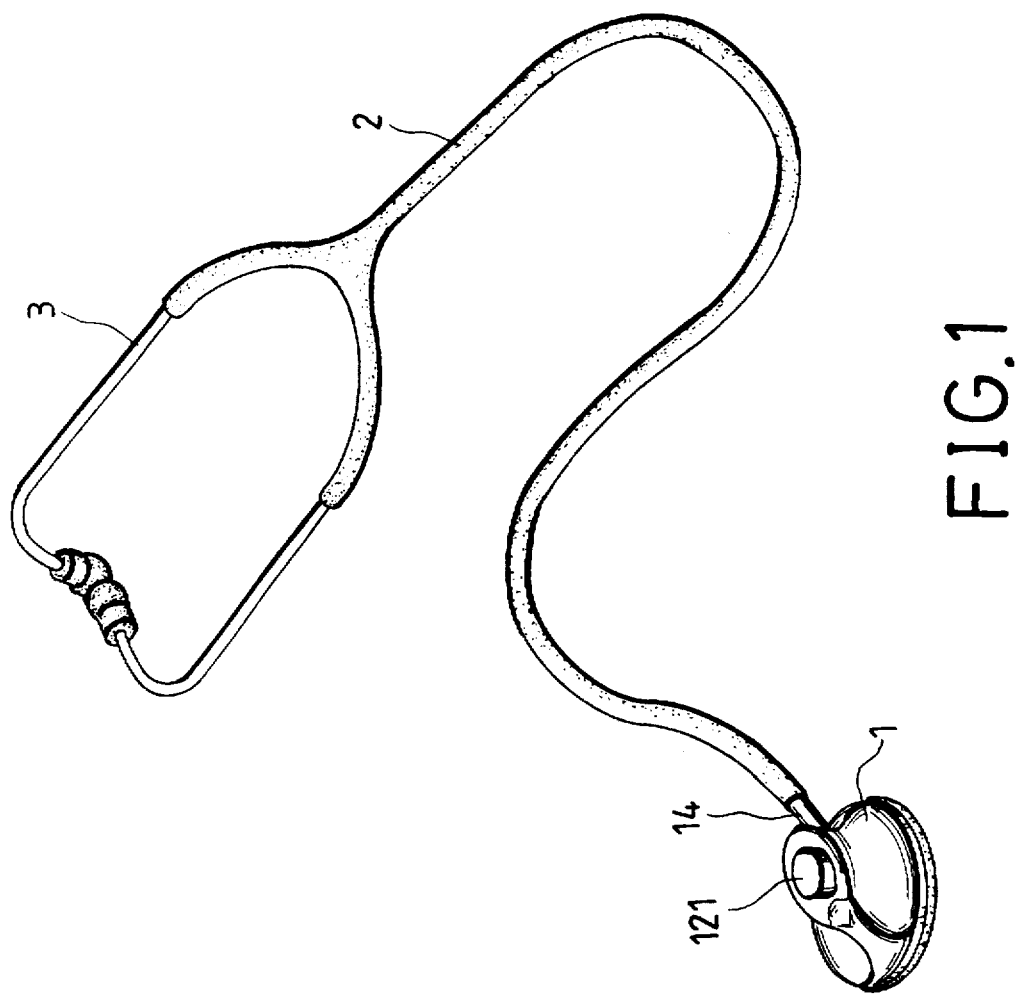
FIG. 1 is a perspective view showing a stethoscope constructed in accordance with the present invention.

With reference to the drawings and in particular to FIG. 1, wherein a stethoscope constructed in accordance with the present invention is shown, the stethoscope comprises a chest piece 1 adapted to receive audio signal from a patient's body (not shown) from which a sound transmitting path defined by is for example a rubber tube 2 extends. A pair of binaurals 3 that are adapted to engage a physician's ears (not shown) are mounted at the opposite end of the rubber tube 2 to apply the audio signal received by the chest piece 1 to the physician's ears.

Figure 2:
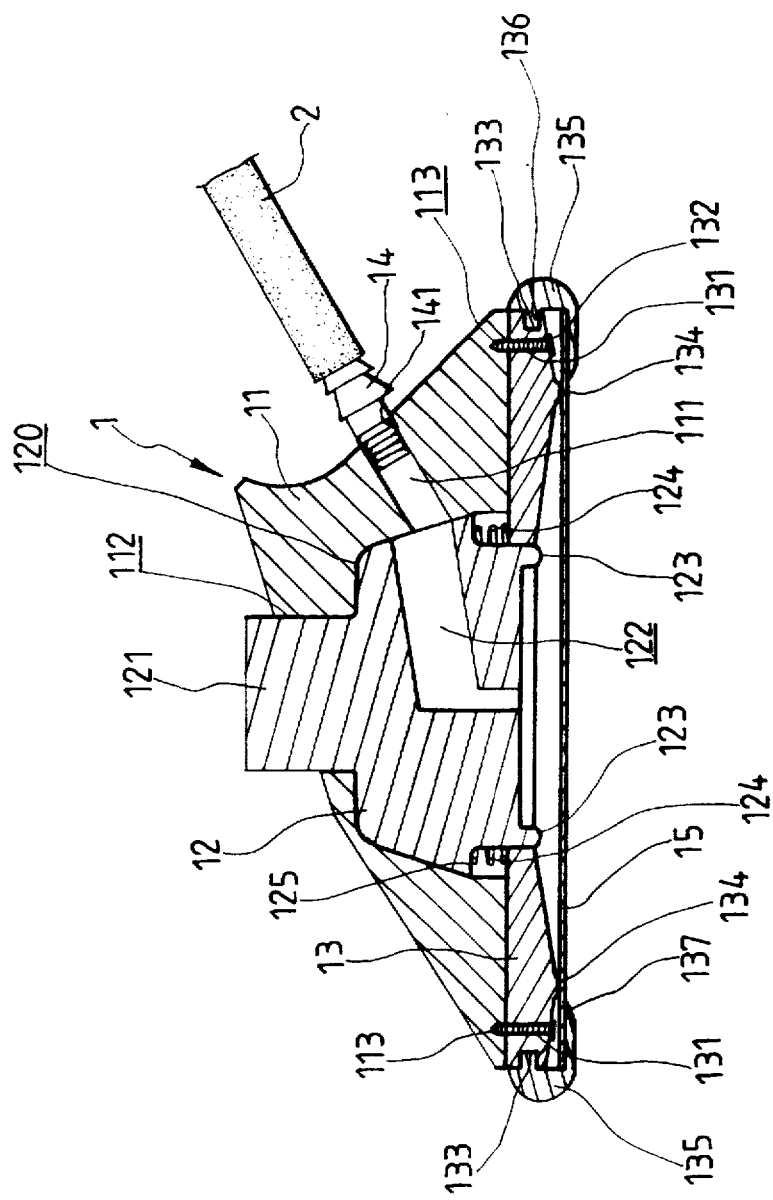
FIG. 2 is a cross-sectional view showing a chest piece constructed in accordance with the present invention in a low frequency mode position.
Figure 3:
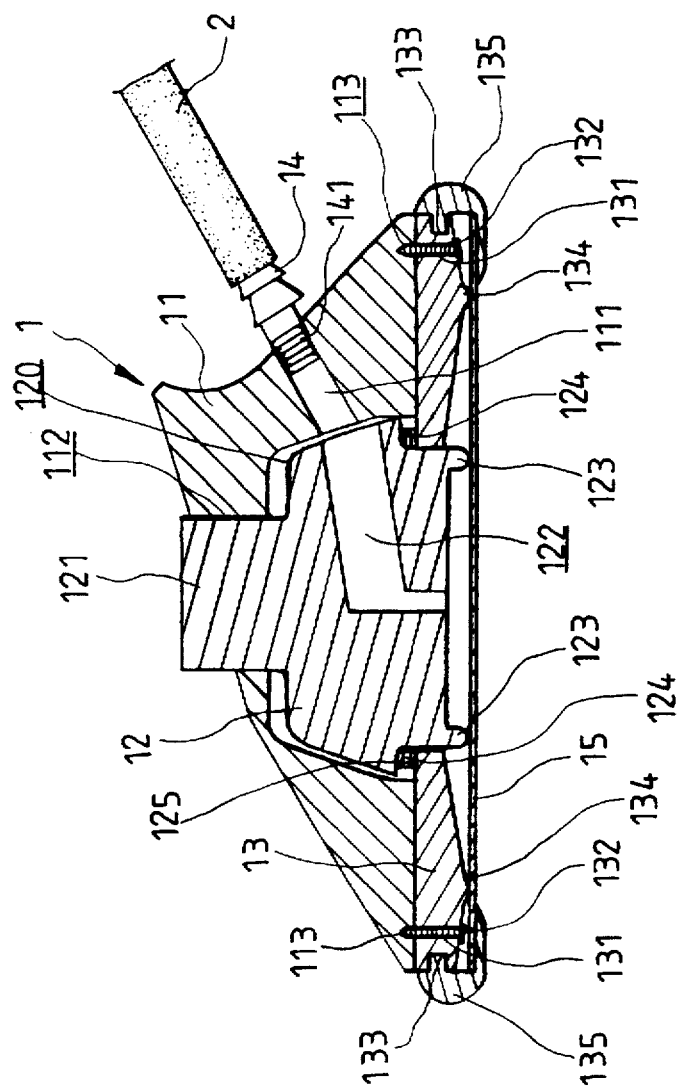
FIG. 3 is a also cross-sectional view of the chest piece of the present invention, but shown in the high frequency mode position.

With further reference to FIGS. 2 and 3, the chest piece 1 comprises a body 11 which may assume a conventional configuration having a substantially flat front side adapted to be placed on the patient's body and an opposite convex back side adapted to be held by the physician's hand (not shown). The body 1 comprises a passage 111 having an opening on the back side of the body 1 to connect to an end of the rubber tube 2. Preferably, the opening of the passage 111 is innerthreaded to threadingly engage external threading 141 of an adaptor 14 which has a free end extending out of the body 11 to be tightly fit over by the end of the rubber tube 2.

The body 1 also has a cavity 120 formed therein and having an opening on the front side thereof to receive a frequency switching member 12. A through hole 112 is formed on the body 1 to extend from the cavity 120 to the back side of the body 1 for receiving therein a pressing button or projection 121 integrally extending from the frequency switching member 12. The pressing button 121 partially extends out of the back side of the body 1 through the hole 112 to be pressed by for example a finger of the physician holding the chest piece 1.

A retainer ring 13 is fixed on the front side of the body 11 by means of for example screws 132 extending through holes 131 formed on the retainer ring 13 and engaging threaded holes 113 provided on the front side of the body 1. The retainer ring 13 defines a bore smaller in size than the opening of the cavity 120 so as to partially overlap and cover the opening of the cavity 120. The frequency switching member 12 that is received within the cavity 120 has a reduced front end sized to be movably received within the bore of the retainer ring 13. The reduced front end defines a circumferential shoulder 125 on the frequency switching member 12, facing the retainer ring 13.

A biasing element, such as a helical spring 124 encompassing the reduced end of the frequency switching member 12 and supported between a portion of the retainer ring 13 that surrounds the bore of the retainer ring 13 and extends into the opening of the cavity 120 and the shoulder 125 of the frequency switching member 12 is provided to bias the frequency switching member 12 toward the back side of the body 1 (which will be referred to as "low frequency mode position" hereinafter), having the pressing button 121 of the frequency switching member 12 projecting out of the back side of the body 1. By depressing the depressing button 121 against the spring 124, the frequency switching member 12 is moved to a position away from the back side and closer to the front side of the body 1 which will be referred to as "high frequency mode position" hereinafter.

The frequency switching member 12 has a circumferential rib 123 formed on the reduced end thereon, defining therein a predetermined area.

A membrane 15 on which vibration may be induced by being placed on and contacting the patient's body is held on the front side of the body 1 by being secured to the retainer ring 13 by means of a holder ring 135 which has an inward extending rib 136 received within a corresponding circumferential slot 133 formed around a lateral side of the retainer ring 13 to be fixed on the retainer ring 13. The holder ring 135 also comprises an inward extending, circumferential flange 137 which partially overlaps the retainer ring 13 with the membrane 15 partially interposed therebetween and thus fixed to the body 1.

The retainer ring 13 comprises a circumferential rib 134 which surrounds the bore of the retainer ring 13 so as to define therein an area greater than the predetermined area defined by the circumferential rib 123 of the reduced end of the frequency switching member 12. The rib 134 is in tight contact engagement with the membrane 15 to separate the membrane 15 from the front side of the body 1, with a space defined therebetween, so that the area defined by the rib 134 provides a first confined zone on the membrane 15 which allows the membrane 15 to vibration in a first, low frequency mode.

The cavity 120, the frequency switching member 12 and the biasing spring 124 are specified to allow the circumferential rib 123 of the reduced end of the frequency switching member 12 to be normally separate from and thus not in contact engagement with the membrane 15 when the frequency switching member 12 is in the low frequency mode position, see FIG. 2.

The circumferential rib 123 of the reduced end of the frequency switching member 12 is brought into contact engagement with the membrane 15 (the high frequency mode position, see FIG. 3) by depressing the depressing button 121 of the frequency switching member 12 against the spring 124 so as to define a second confined zone on the membrane 15 which is smaller than the first confined zone, allowing the membrane 15 to vibrate at a second, high frequency mode. Since the area defined by the circumferential rib 123 is smaller than that defined by the circumferential rib 134 so that a higher frequency may be generated by the membrane 15 when in contact engagement with the circumferential rib 123.

The frequency switching member 12 is provided with a sound transmitting channel 122 which is in communication with the space defined between the membrane 15 and the front side of the body 1 and extends to the passage 111 so as to transmit the frequency from the membrane 15 to the binaurals 3.

The depressing button 121 provides a simple and efficient manner to switch the operation of the stethoscope in accordance with the present invention between high frequency mode and lower frequency mode by depressing the button 121 to bring the inner circumferential rib 123 into contact with the membrane 15.

It is apparent that although the invention has been described in connection with the preferred embodiment, it is contemplated that those skilled in the art may make changes to certain features of the preferred embodiment without altering the basic concept of the invention and without departing from the spirit and scope of the invention as defined in the appended claims.

What is claimed is:

1. A stethoscope comprising a pair of binaurals and a chest piece with a sound transmitting path connected therebetween, the chest piece comprising:

a body having a substantially flat front side adapted to be placed on a patient's body and a convex back side adapted to be held by a hand with the sound transmitting path extending from the back side thereof to the binaurals, the body having a cavity formed therein with an opening on the front side, a through hole extending from the cavity to the back side of the body;

a frequency switching member movably received within the cavity between a low frequency mode position closer to the back side of the body and a high frequency mode position away from the back side of the body and closer to the opening of the cavity on the front side of the body, the frequency switching member having a projection extending through the through hole of the body to at least partially project out of the back side of the body to be accessible by the hand, the frequency switching member being provided with a circumferential rib on a front side thereof which defines a predetermined area;

a retainer ring fixed to the front side of the body, having a bore smaller is size than the opening of the cavity and partially overlapping the opening of the cavity to retain the frequency switching member within the cavity, the bore of the retainer ring being sized to allow the circumferential rib of the frequency switching member to move therethrough in moving from the low frequency mode position to the high frequency mode position, the retainer ring comprising a circumferential rib surrounding the bore and thus the circumferential rib of the frequency switching member so as to define an area greater than the predetermined area defined by the circumferential rib of the frequency switching member;

a biasing element provided between the frequency switching member and the retainer ring so as to bias the frequency switching member toward the low frequency mode position to have the projection thereof extending out of the back side of the body through the through hole of the body; and a membrane fixed to the retainer ring to be in contact engagement with the circumferential rib of the retainer ring which separates the membrane from the front side of the body and defines thereon a first confined zone providing a first, low frequency vibration mode of the membrane; and wherein the frequency switching member is movable from the low frequency mode position toward the high frequency mode position by depressing the projection thereof against the biasing element so as to bring the circumferential rib of the frequency switching member into contact engagement with the membrane to define thereon a second confined zone providing a second, high frequency vibration mode of the membrane.

2. The stethoscope as claimed in claim 1, wherein the body comprises a passage in communication with the sound transmitting path and wherein the frequency switching member comprises a channel extending from the space between the membrane and the front side of the body to the passage.

3. The stethoscope as claimed in claim 2, wherein the passage comprises an inner-threaded opening to which an externally threaded adaptor is mounted, the sound transmitting path being connected to the adaptor.

4. The stethoscope as claimed in claim 1, wherein the sound transmitting path comprises a rubber tube.

5. The stethoscope as claimed in claim 1, wherein the frequency switching member comprises a reduced front end sized to be movable through the bore of the retainer ring with the circumferential rib of the frequency switching member provided thereon, the reduced front end defining a circumferential shoulder on the frequency switching member and wherein the biasing element comprises a helical spring encompassing the reduced end of the frequency switching member and supported between the shoulder and a portion of the retainer ring that overlaps the cavity opening of the body.

6. The stethoscope as claimed in claim 1, wherein the retainer ring comprises a circumferential slot formed on a lateral side thereof, a holder ring having an inward extending rib received within the slot to fix the holder ring on the retainer ring, the holder ring further comprising an inward extending flange partially overlapping the retainer ring to interpose and thus fix the membrane therebetween.

\* \* \* \* \*